(12) United States Patent
Shelly et al.

(10) Patent No.: US 10,137,266 B2
(45) Date of Patent: Nov. 27, 2018

(54) PATIENT-VENTILATOR DYSSYNCHRONY DETECTION

(75) Inventors: Benjamin Irwin Shelly, Pittsburgh, PA (US); Sankarasubrahmani Uday Shankar, Chennai (IN); Michael T. Kane, Harrison City, PA (US); Gregory Delano Matthews, Pittsburgh, PA (US); Heather Dawn Ressler, New Alexandria, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1215 days.

(21) Appl. No.: 13/202,100

(22) PCT Filed: Jan. 22, 2010

(86) PCT No.: PCT/IB2010/050294
§ 371 (c)(1),
(2), (4) Date: Aug. 18, 2011

(87) PCT Pub. No.: WO2010/097717
PCT Pub. Date: Sep. 2, 2010

(65) Prior Publication Data
US 2011/0297155 A1    Dec. 8, 2011

Related U.S. Application Data

(60) Provisional application No. 61/155,363, filed on Feb. 25, 2009.

(51) Int. Cl.
*A61M 16/00* (2006.01)

(52) U.S. Cl.
CPC ... *A61M 16/024* (2017.08); *A61M 2016/0015* (2013.01)

(58) Field of Classification Search
CPC .............. A61M 16/00; A61M 16/0003; A61M 16/0057; A61M 16/0066; A61M 16/0069;
(Continued)

(56) References Cited

U.S. PATENT DOCUMENTS

| | | | | | |
|---|---|---|---|---|---|
| 4,340,044 | A | * | 7/1982 | Levy | A61M 16/00 128/204.21 |
| 5,146,918 | A | * | 9/1992 | Kallok | A61N 1/3601 607/2 |

(Continued)

FOREIGN PATENT DOCUMENTS

| | | |
|---|---|---|
| JP | 2008503278 A | 2/2008 |
| WO | WO200228460 | 4/2002 |

(Continued)

*Primary Examiner* — Lynne Anderson
*Assistant Examiner* — Joseph D Boecker
(74) *Attorney, Agent, or Firm* — Michael W. Haas

(57) ABSTRACT

A method of detecting dyssynchrony between a patient and a pressure support system includes receiving patient flow data relating to a flow of gas provided to the patient by the pressure support system, receiving an I/E state signal representing a respiratory phase of the patient as determined by the pressure support system, and analyzing the patient flow data and the I/E state signal and declaring a dyssynchrony for a breath based on at least one of the patient flow data and the I/E state signal. The method includes determining whether at least one of a number of predetermined criterion is satisfied based on at least one of the patient flow data and the I/E state signal, and declaring the dyssynchrony for the breath if it is determined that at least one of the number of predetermined criterion is satisfied.

39 Claims, 10 Drawing Sheets

(58) Field of Classification Search
CPC ............. A61M 16/021; A61M 16/022; A61M 16/024; A61M 2016/0015; A61M 2016/0018; A61M 2016/003; A61M 2016/0033; A61M 2016/0039; A61M 2016/0051; A61B 5/087

See application file for complete search history.

(56) References Cited

U.S. PATENT DOCUMENTS

| | | | |
|---|---|---|---|
| 5,148,802 A * | 9/1992 | Sanders et al. | 128/204.18 |
| 5,239,995 A | 8/1993 | Estes et al. | |
| 5,303,698 A * | 4/1994 | Tobia | A61M 16/024 |
| | | | 128/204.21 |
| 5,313,937 A | 5/1994 | Zdrojkowski | |
| 5,433,193 A | 7/1995 | Sanders et al. | |
| 5,485,850 A * | 1/1996 | Dietz | 600/529 |
| 5,632,269 A | 5/1997 | Zdrojkowski | |
| 5,803,065 A | 9/1998 | Zdrojkowski et al. | |
| 5,803,066 A * | 9/1998 | Rapoport et al. | 128/204.23 |
| 6,029,664 A | 2/2000 | Zdrojkowski et al. | |
| 6,148,814 A * | 11/2000 | Clemmer et al. | 128/200.24 |
| 6,213,119 B1 * | 4/2001 | Brydon | A61M 16/024 |
| | | | 128/204.18 |
| 6,237,592 B1 * | 5/2001 | Surjadi et al. | 128/204.21 |
| 6,345,619 B1 * | 2/2002 | Finn | A61M 16/00 |
| | | | 128/204.18 |
| 6,532,960 B1 | 3/2003 | Yurko | |
| 6,606,993 B1 * | 8/2003 | Wiesmann et al. | 128/204.23 |
| 6,633,775 B1 * | 10/2003 | Bernard | 600/428 |
| 6,640,806 B2 | 11/2003 | Yurko | |
| 6,837,242 B2 | 1/2005 | Tounes | |
| 6,920,875 B1 | 7/2005 | Hill et al. | |
| 7,044,129 B1 * | 5/2006 | Truschel et al. | 128/204.23 |
| 9,027,552 B2 * | 5/2015 | Angelico | A61M 16/0051 |
| | | | 128/204.18 |
| 9,295,803 B2 * | 3/2016 | Korten | A61M 16/0051 |
| 2002/0053345 A1 * | 5/2002 | Jafari | A61M 16/00 |
| | | | 128/204.23 |
| 2003/0050568 A1 * | 3/2003 | Green | A61M 16/0051 |
| | | | 600/538 |
| 2003/0213490 A1 * | 11/2003 | Righetti | A61M 16/0677 |
| | | | 128/204.18 |
| 2004/0050387 A1 * | 3/2004 | Younes | A61M 16/026 |
| | | | 128/204.18 |
| 2004/0172077 A1 * | 9/2004 | Chinchoy | A61N 1/3622 |
| | | | 607/17 |
| 2006/0020294 A1 * | 1/2006 | Brockway et al. | 607/17 |
| 2007/0221218 A1 * | 9/2007 | Warden | A61M 15/0045 |
| | | | 128/203.15 |
| 2007/0270671 A1 * | 11/2007 | Gal | A61B 5/0002 |
| | | | 600/301 |
| 2007/0293781 A1 * | 12/2007 | Sims | A61B 5/1135 |
| | | | 600/534 |
| 2008/0110461 A1 * | 5/2008 | Mulqueeny | A61M 16/00 |
| | | | 128/204.23 |
| 2008/0283060 A1 | 11/2008 | Bassin | |
| 2008/0302364 A1 | 12/2008 | Garde et al. | |
| 2008/0314384 A1 * | 12/2008 | Harris | A61M 15/0028 |
| | | | 128/203.15 |
| 2009/0050154 A1 * | 2/2009 | Strothmann | A61M 16/0051 |
| | | | 128/204.23 |
| 2009/0112083 A1 * | 4/2009 | Aulbach | A61B 5/416 |
| | | | 600/413 |
| 2010/0016694 A1 * | 1/2010 | Martin | A61M 16/0051 |
| | | | 600/324 |
| 2010/0252038 A1 * | 10/2010 | Lagerborg | A61B 5/0488 |
| | | | 128/204.23 |
| 2012/0291785 A1 * | 11/2012 | Ramanan | A61M 16/0051 |
| | | | 128/204.23 |

FOREIGN PATENT DOCUMENTS

| | | |
|---|---|---|
| WO | WO2004002561 | 1/2004 |
| WO | WO2008000017 A1 | 1/2006 |
| WO | WO2009026582 | 2/2009 |

* cited by examiner

PATIENT-VENTILATOR DYSSYNCHRONY DETECTION

This patent application claims the priority benefit under 35 U.S.C. § 119(e) of U.S. Provisional Application No. 61/155,363 filed on Feb. 25, 2009, the contents of which are herein incorporated by reference.

The present invention relates to positive airway pressure support systems, and, more particularly, to a method for detecting dyssynchrony between a patient and a pressure support system, such as a conventional ventilator.

It is known to utilize a conventional ventilator or pressure support system to deliver a fluid, such as oxygen, air, or another oxygen or breathing gas mixture, to an airway of patient to augment or substitute the patient's own ventilatory effort. One basic form of pressure support therapy that may be provided by a ventilator is bi-level positive pressure therapy in which the pressure of gas delivered to the patient varies with the patient's breathing cycle.

In a bi-level pressure support system, an inspiratory positive airway pressure (IPAP) is provided during a patient's inspiratory phase of the breathing cycle and an expiratory positive airway pressure (EPAP) is provided during the expiratory phase. The EPAP is lower than the IPAP so that the patient exhales against a relatively low pressure as compared to the IPAP pressure, thereby increasing the comfort to the patient. The BiPAP® family of pressure support devices manufactured by Respironics, Inc. of Murrysville, Pa., are examples of pressure support device that provide this bi-level form of pressure support therapy. In addition, several U.S. patents describe this bi-level pressure support system in detail, including U.S. Pat. Nos. 5,433,193; 5,313,937; 5,239,995; 5,148,802; 6,532,960; and 6,640,806, all of which are hereby expressly incorporated herein by reference as if set forth in their entirety herein.

It is further known to operate a conventional ventilator in a variety of modes to control the four basic operations of a ventilator, which are: 1) the trigger point, which is the transition from the expiratory to the inspiratory phase of the ventilatory cycle; 2) the inspiratory phase where the ventilator delivers the flow of breathing gas; 3) the cycle point, which is the transition from the inspiratory phase to the expiratory phase, and 4) the expiratory phase. There are four primary variables or parameters that are typically monitored and used to control how a ventilator performs one or more of these four operations. These variables are the volume, pressure, flow of fluid to or from the patient, and time.

In a typical life support situation, where there is substantially no spontaneous respiratory effort by the patient, a controlled mode of ventilation is provided, where the ventilator assumes full responsibility for ventilating the patient. In this mode of ventilation, the trigger and cycle point of the ventilator are determined based on time. In other situations, where the patient exhibits some degree of spontaneous respiratory effort, an assist mode or a support mode of ventilation is typically provided. Both of these modes of ventilation cause the ventilator to augment or assist in the patient's own respiratory efforts. In the assist mode, the determination of the ventilator trigger point is based on the action of the patient and the determination of the cycle point is determined based on time. In the support mode, both the trigger and the cycle points are patient based and not based on time. It is also known to use a combination of these two modes, referred to as an assist/control mode of ventilation. In this mode of ventilation, the ventilator triggers an inspiratory flow (a backup breath) only if the patient fails to initiate a respiratory effort for a period of time. Thus, the trigger point is based on either a patient action or on time, if there is no patient action within a certain period of time.

In the assist, support, and assist/control modes of ventilation, it is important that the operation of the ventilator is synchronized with the patient's spontaneous respiratory effort, so that the ventilator triggers the inspiratory flow of breathing gas at or near the time the patient begins his or her inspiratory effort, and cycles to the expiratory phase of the breathing pattern at an appropriate time, preferably when the patient begins his or her expiratory phase of the breathing cycle. Conventional ventilators operating in an assist, support, or assist/control mode of ventilation typically monitor a patient parameter, such as the pressure, flow, or volume, and use this monitored parameter as a variable in determining when to spontaneously trigger the delivery of the inspiratory flow. Typically, the monitored parameter is compared to a threshold, and if the threshold is exceeded, the transition from expiration to inspiration (trigger) or from inspiration to expiration (cycle) is initiated.

Dyssynchrony is the condition where the patient's respiratory drive and the breaths generated by the ventilator are out of sync with one another. Dyssynchrony can arise due to a variety of reasons, such as, without limitation, fixed backup rates, timed breaths triggered on flow-based criteria without accounting for ventilatory needs (e.g. ventilating through necessary longer respiratory pauses), and poor triggering, among others. Dyssynchrony is uncomfortable for the patient and can be described as fighting the ventilator. Often, dyssynchrony will be noted by the patient when the ventilator increases pressure while the patient is trying to exhale or decreases the pressure when the patient is trying to inhale. In addition to patient discomfort, dyssynchrony may cause the ventilator to make erroneous judgments regarding important patient parameters (e.g., tidal volumes, peak inspiratory flows, breath rate, etc.) and either make poor decisions based on those judgments or provide invalid information to a physician or another caregiver.

In one embodiment, a method of detecting dyssynchrony between a patient and a pressure support system is provided that includes receiving patient flow data relating to a flow of gas provided to the patient by the pressure support system, obtaining an I/E state signal representing a respiratory phase of the patient, and analyzing the patient flow data and the I/E state signal and declaring a dyssynchrony for a breath based on at least one of the patient flow data and the I/E state signal. The I/E state signal may be generated by the pressure support system. Also, the receiving, obtaining and analyzing may be performed by the pressure support system. Alternatively, the receiving patient flow data may comprise receiving patient flow data in a dyssynchrony detection apparatus separate from the pressure support system, the obtaining an I/E state signal may comprise receiving the I/E state signal from the pressure support system in the dyssynchrony detection apparatus, and the analyzing may be performed by the dyssynchrony detection apparatus. In another embodiment, the obtaining an I/E state signal comprises receiving pressure data relating to a pressure of the flow of gas provided to the patient by the pressure support system and generating the I/E state signal based on the pressure data. The receiving patient flow data may comprise receiving the patient flow data in a dyssynchrony detection apparatus separate from the pressure support system, the receiving pressure data and the generating the I/E state signal may comprise receiving the pressure data in the dyssynchrony detection apparatus and generating the I/E state signal in the dyssynchrony detection apparatus, and the analyzing may be performed by the dyssynchrony detection apparatus.

In a particular embodiment, the method further includes determining, based on at least one of the patient flow data and the I/E state signal, whether at least one of a number of predetermined criterion is satisfied, wherein the declaring comprises declaring the dyssynchrony for the breath if it is determined that at least one of the number of predetermined criterion is satisfied. The number of predetermined criterion may include one or more of, or all of: (i) a number of volume qualified flow slope reversals in the patient flow data for the breath exceeding a predetermined number; (ii) an incremental tidal volume during at least a portion of an expiratory phase of the breath as indicated by the I/E state signal exceeding a predetermined positive value; (iii) an absolute value of a tidal volume during the breath exceeds a predetermined value; (iv) a length of an expiratory phase of the breath as indicated by the I/E state signal does not exceed a predetermined percentage of a length of the an inspiratory phase of the breath as indicated by the I/E state signal (or, alternatively, a predetermined duration); and (v) a tidal volume during an inspiratory phase of the breath as indicated by the I/E state is less than a predetermined negative value.

In another embodiment, the declaring includes declaring a plurality of dyssynchronies for a plurality of breaths based on the patient flow data and the I/E state signal, and the method further includes generating a dyssynchrony flag waveform based on the plurality of dyssynchronies. The method may also further include modifying the operation of the pressure support system based on the plurality of dyssynchronies and/or detecting information about a condition of the patient based on the plurality of dyssynchronies. Alternatively, the method may include modifying the operation of the pressure support system based on the declared dyssynchrony and/or detecting information about a condition of the patient based on the declared dyssynchrony.

In one particular embodiment, the declaring includes declaring a dyssynchrony for a breath based on both the patient flow data and the I/E state signal.

A pressure support system is also provided that includes a pressure generating system adapted to produce a flow of gas, a patient circuit operatively coupled to the pressure generating system to deliver the flow of gas to an airway of a patient, and a controller operatively coupled to the pressure generating system. The controller is adapted to detect dyssynchrony between the patient and the pressure support system by receiving patient flow data relating to the flow of gas provided to the patient by the pressure support system, receiving an I/E state signal representing a respiratory phase of the patient as determined by the pressure support system, and analyzing the patient flow data and the I/E state signal and declaring a dyssynchrony for a breath based on at least one of the patient flow data and the I/E state signal according to one or more of the embodiments just described.

An apparatus for detecting dyssynchrony between a patient and a pressure support system is also provided that includes a housing separate from the pressure support system, and a controller provided within the housing and operatively coupled to the pressure generating system, the controller being adapted to detect dyssynchrony between the patient and the pressure support system by receiving patient flow data relating to a flow of gas provided to the patient by the pressure support system, obtaining an I/E state signal representing a respiratory phase of the patient (either form the pressure support system or by generating the signal based on received patient pressure data), and analyzing the patient flow data and the I/E state signal and declaring a dyssynchrony for a breath based on at least one of the patient flow data and the I/E state signal according to one or more of the embodiments just described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
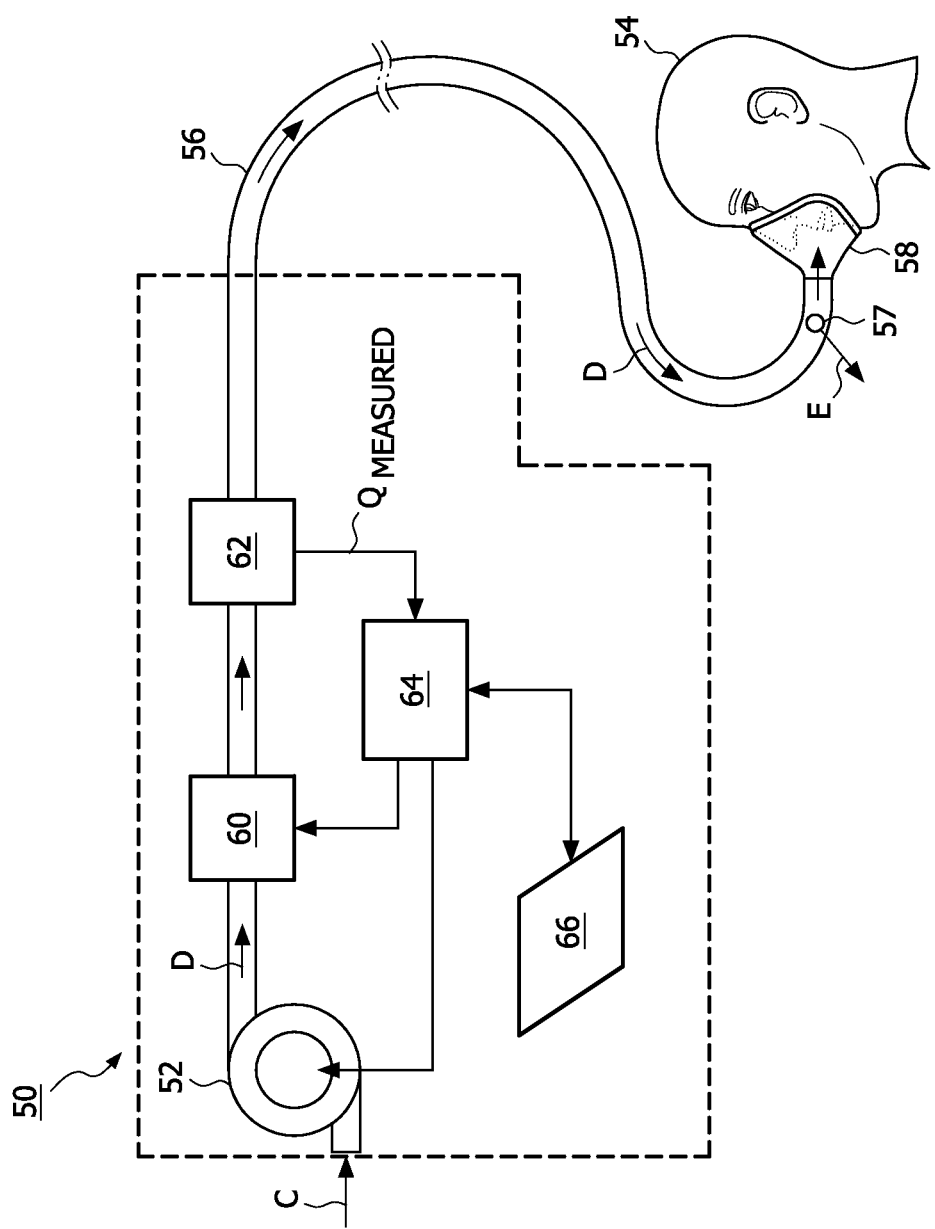
FIG. 1 is a schematic diagram of a pressure support system according to one particular, non-limiting embodiment of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As described in greater detail herein, the present invention provides a methodology for determining when dyssynchrony is occurring during therapy provided by a pressure support system (e.g., a ventilator) so that that information can be used to, for example, modify the operation of the pressure support system (e.g., without limitation, change parameters, remove data points from trends, change backup breath rate, and/or modify internal parameters) or detect information about a patient (e.g., without limitation, patient over/under-ventilated, patient distress, patient sleep state (awake v. asleep), etc.).

In determining when dyssynchrony is occurring, the methodology in one particular embodiment employs the following data generated by the pressure support system: (i) an effective patient flow waveform which represents patient flow sampled at a predetermined sample rate such as, without limitation, 10 samples/second, and (ii) an I/E state signal, which indicates the perceived respiratory state of the patient (i.e., inspiratory phase or expiratory phase) as determined by the pressure support system (hence, the I/E state signal identifies transitions between the states). Further, the methodology contemplates outputting a dyssynchrony flag waveform wherein a first value (e.g., a 1) represents detected dyssynchrony and a second value (e.g., a 0) represents no dyssynchrony. In one particular, non-limiting example, the dyssynchrony condition (e.g., represented by a 1) is output from the time the condition is detected within a breath to a point 100 ms after the onset of the next breath, and no dyssynchrony (e.g., represented by a 0) is output at all other times. In addition, the dyssynchrony information may be output to a user interface and/or to external media.

FIG. 1 is a schematic diagram of pressure support system 50 according to one particular, non-limiting embodiment of the invention which will be used herein to illustrate various embodiments of the present invention. Referring to FIG. 1, pressure support system 50 includes gas flow generator 52, such as a blower used in a conventional CPAP or bi-level pressure support device, which receives breathing gas, generally indicated by arrow C, from any suitable source, e.g., a pressurized tank of oxygen or air or other gas or gas mixture, the ambient atmosphere, or a combination thereof. Gas flow generator 52 generates a flow of breathing gas, such as air, oxygen, or a mixture thereof, for delivery to an airway of patient 54 at relatively higher and lower pressures, i.e., generally equal to or above ambient atmospheric pressure.

The pressurized flow of breathing gas, generally indicated by arrow D from gas flow generator 52, is delivered via delivery conduit 56 to breathing mask or patient interface 58 of any known construction, which is typically worn by or otherwise attached to patient 54 to communicate the flow of breathing gas to the airway of patient 54. Delivery conduit 56 and patient interface device 58 are typically collectively referred to as a patient circuit. In an exemplary embodiment, patient interface 58 includes a pressure sensor operatively coupled to controller 64 for measuring the pressure of gas that is delivered to patient 54.

Pressure support system 50 shown in FIG. 1 is what is known as a single-limb system, meaning that the patient circuit includes only delivery conduit 56 connecting patient 54 to pressure support system 50. As such, exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal mask. It is to be understood, however, that patient interface 58 can include a nasal/oral mask, full face mask, nasal cannula, nasal pillows, tracheal tube, endotracheal tube, or any other device that provides a suitable gas flow communicating function. Also, for purposes of the present invention, the phrase "patient interface" can include delivery conduit 56 and any other structures that connect the source of pressurized breathing gas to patient 54.

In the illustrated embodiment, pressure support system 50 includes a pressure controller in the form of valve 60 provided in delivery conduit 56. Valve 60 controls the pressure of the flow of breathing gas from flow generator 52 delivered to patient 54. For present purposes, flow generator 52 and valve 60 are collectively referred to a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes flow sensor 62 that measures the flow of the breathing gas within delivery conduit 56. In the particular embodiment shown in FIG. 1, flow sensor 62 is interposed in line with delivery conduit 56, most typically downstream of valve 60. Flow sensor 62 generates a flow signal $Q_{MEASURED}$ that is provided to controller 64 and is used by controller 64 to determine the flow of gas at patient 54, which may then be used to generate the effective patient flow waveform employed in the present invention as described elsewhere herein. Of course, other techniques for measuring the respiratory flow of patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

Controller 64 may be, for example, a microprocessor, a microcontroller or some other suitable processing device, that includes or is operatively coupled to a memory (not shown) that provides a storage medium for data and software executable by controller 64 for controlling the operation of pressure support system 50, including monitoring characteristics of patient respiration and controlling the flow of breathing gas based thereon as described in greater detail herein. Finally, input/output device 66 is provided for setting various parameters used by pressure support system 50, as well as for displaying and outputting information and data to a user, such as a clinician or caregiver.

In an exemplary, non-limiting embodiment of the present invention, pressure support system 50 essentially functions as a bi-level pressure support system, and, therefore, includes all of the capabilities necessary in such systems in order to provide separate IPAP and EPAP levels to patient 54. This includes receiving the necessary parameters, via input commands, signals, instructions or other information, for providing a bi-level pressure, such as maximum and minimum IPAP and EPAP settings. The flow signal $Q_{MEASURED}$ from flow sensor 62 is also provided to controller 64, which controls the pressure generating system to output the desired inspiratory and expiratory waveforms.

Typically, carrying out the pressure support operation includes estimating or determining the actual patient flow based on the flow signal $Q_{MEASURED}$, determining whether the patient is in the inspiratory or expiratory phase of the respiratory cycle and providing an I/E state signal (binary in form) indicative of the perceived respiratory state of patient 54 (I representing inspiratory phase and E representing expiratory phase), and triggering and cycling pressure support system 50. In addition, in an exemplary embodiment, pressure support system 50 is adapted to implement an automatic backup process wherein if a central apnea or cessation of respiratory effort is detected for a period of time, then a "machine breath" or "backup breath" is automatically delivered to the patient by pressure support system 50, thus ventilating the lungs. Thus, pressure support system 50 is able to provide control, assist, support, and assist/control modes of ventilation.

In an exemplary embodiment of the present invention, which is a single-limb system, controller 64 estimates the leakage of gas from the pressure support system using any conventional technique and incorporates this leak estimation into the determination of the actual patient flow. This leak estimation is required in a single-limb system, because a single-limb system includes a known leak through the exhaust vent as well as other unknown leaks, such as leaks at the patient contact site of the patient interface and at various conduit couplings on the patient circuit. In a two-limb system, leak estimation may not be required, because a flow sensor is typically provided at the exhaust vent to measure, directly, the flow of exhaust gas. In such a system, the patient flow can be determined by subtracting the measured exhaust flow from the measured flow delivered to the patient. It can be appreciated that leak detection can be performed in a two-limb system to increase the accuracy of the patient flow determination.

U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., U.S. Pat. No. 6,029,664 to Zdrojkowski et al., and U.S. Pat. No. 6,920,875 to Hill et al., the contents of each of which are incorporated herein by reference, describe how to accomplish the necessary functions in order to provide separate IPAP and EPAP levels to the patient. These functions include techniques for detecting and estimating leak, and techniques for detecting the respiratory state of a patient, and managing, e.g., triggering and cycling, the bi-level delivery of breathing gas to the patient in the presence of leaks. Thus, a detailed discussion of these functions is omitted from the present application for the sake of simplicity and brevity.

The present invention provides a method that is implemented in controller 64 of pressure support system 50 wherein dyssynchrony between pressure support system 50 and patient 54 is able to be determined based on an effective patient flow waveform generated by controller 64 (based on the flow signal $Q_{MEASURED}$ and representing patient flow) and an I/E state signal generated by controller 64. In an exemplary embodiment, the occurrence of dyssynchrony is determined by controller 64 by examining the portions of the effective patient flow waveform and the I/E state signal that are associated with individual breaths and determining whether one or more of a number of predetermined criteria is present. The particular criteria for one particular embodiment are described below in connection with FIGS. 2A-6B.

Figure 2A:
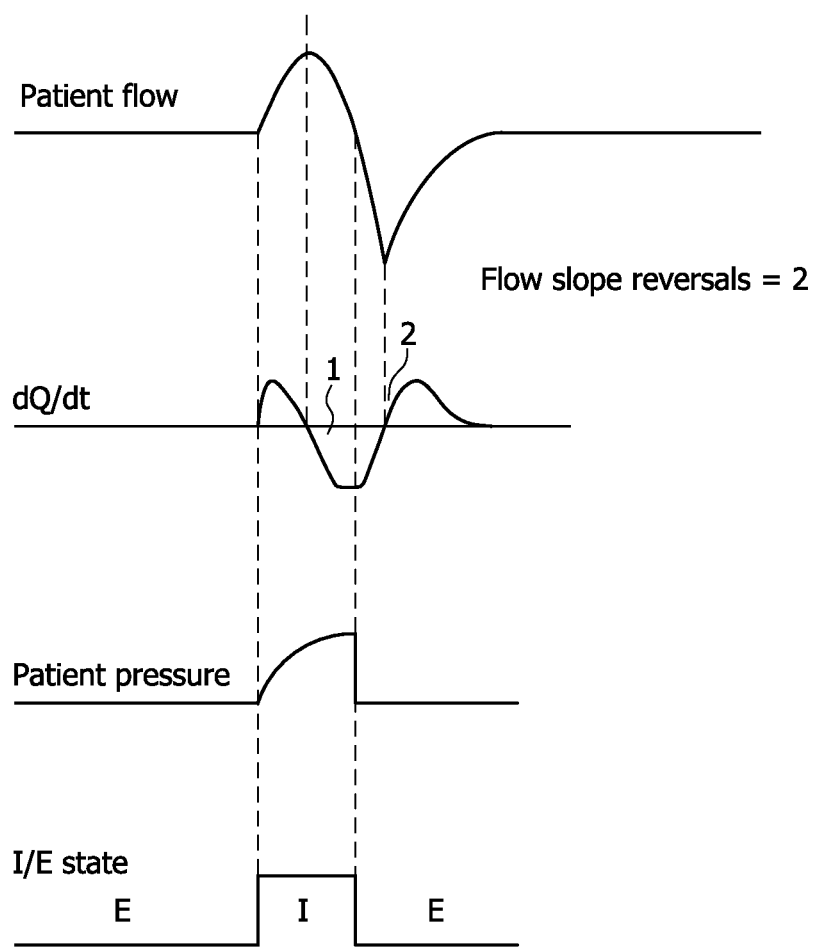
FIGS. 2A, 2B and 2C show an effective patient flow waveform, dQ/dt, a patient pressure waveform and an I/E state signal for a normal breath, a flow-limited breath, and a dyssynchronous breath, respectively which illustrate a first criterion for detecting dyssynchrony according to an embodiment the invention.
Figure 2B:
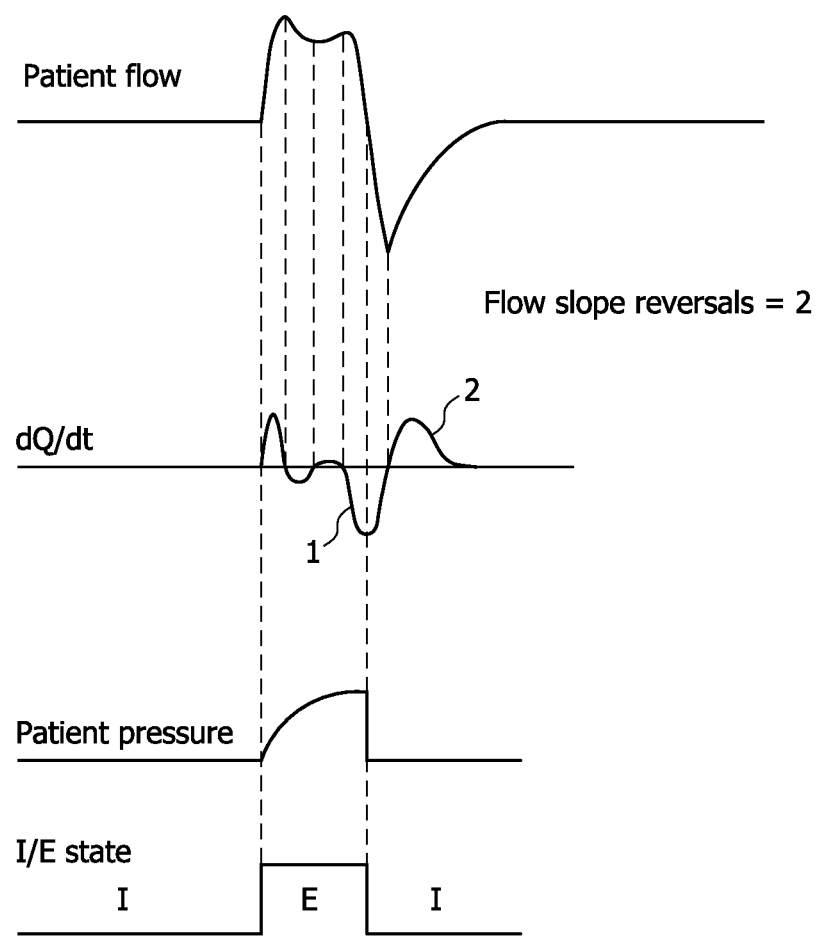
Figure 2C:
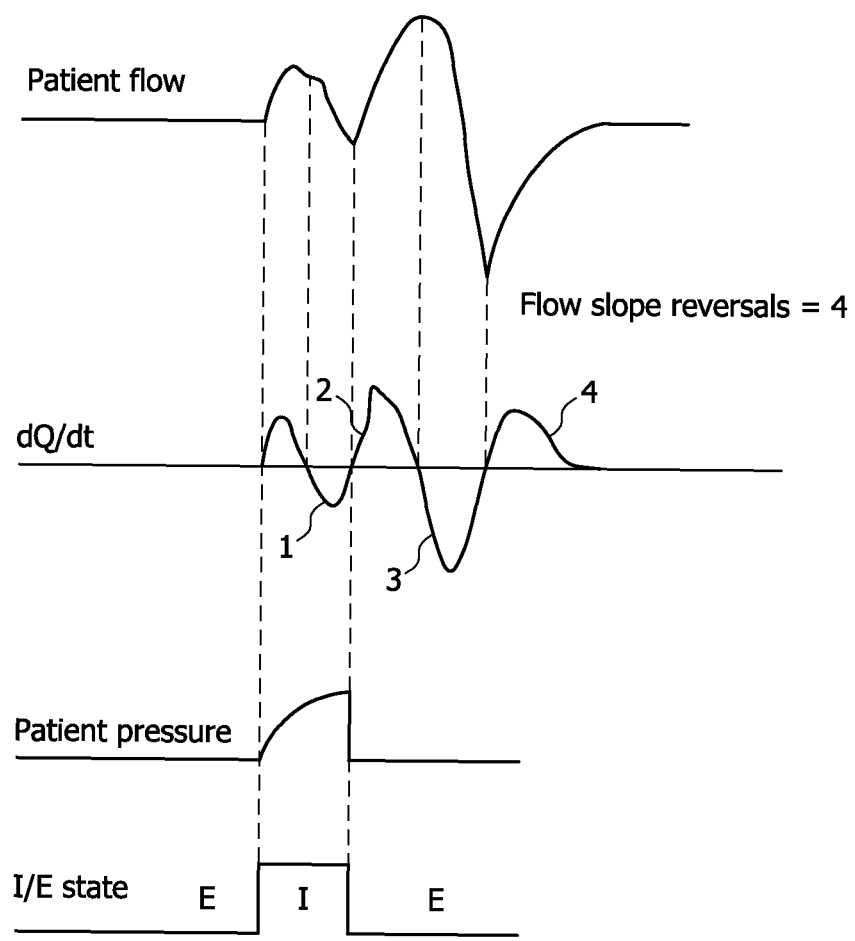

The first criterion is demonstrated in FIGS. 2A, 2B and 2C and is based on the number of flow slope (i.e., dQ/dt) reversals that are present in a given breath (as indicated by the I/E state signal). The term "reversal" as used herein means change in its sign as in from positive to negative or vice-versa. Thus, the slope of a rising signal is positive and that of a falling signal negative. These are regardless of the absolute values of the signal (for example, the flow can go from −20 LPM to −5 LPM in 10 ms and the slope would be positive whereas the flow can go from +20 to +5 in 10 ms and the slope would be negative). A flat signal has zero-slope. The method described herein ignores zero-slope sections or points and waits for a true reversal in the sign. More specifically, the number of flow slope reversals (which appear as dips, glitches as well as larger swings on the patient flow waveform) in a breath (as indicated by the I/E state signal; i.e., the beginning of one I, which signals the start of a breath, to the beginning of the next I, which signals the start of a next breath) is determined. If that number exceeds a certain empirically determined number, then a dyssynchrony condition is declared because such a situation indicates at least some patient respiratory drive opposing harmony with pressure support system 50. The certain empirically determined number may, for example and without limitation, be two, which number would account for normal slope reversals (one after the peak of inspiration and one after the trough of expiration).

In order to distinguish between slope reversals caused by true dyssynchrony and those caused by flow limited breathing, a volume based test is used. The basis for a volume-based test is that strong respiratory drive-related changes to patient flow as occurs in dyssynchrony are much larger as well as more rapid than the small dips seen due to flow limited breathing. If the change in volume within a certain empirically determined period is below a certain empirically determined volume threshold, then that particular flow slope reversal is ignored. For ease of description herein and in the claims, flow slope reversals that fulfill the volume based test described above shall be referred to herein as "volume qualified flow slope reversals". That empirically determined volume may be, without limitation, −21 ml for negative slopes and 18 ml for positive slopes. The empirically determined period may be, without limitation, 200 milliseconds. It should be understood, however, that other empirically determined numbers are possible within the scope of the present invention for all such above mentioned numbers.

FIG. 2A shows the effective patient flow waveform, the patient pressure waveform (the pressure provided by pressure support system 50), dQ/dt, and the I/E state signal for a normal breath, where flow slope reversals are numbered and equal two. FIG. 2B shows the effective patient flow waveform, the patient pressure waveform, dQ/dt, and the I/E state signal for a flow-limited breath, where flow slope reversals are numbered and equal two. This case is provided to illustrate the situation where the small dips at the peak of inspiration caused by flow-limited breathing, cause short-term slope changes but these slope changes do not fulfill the volume criteria mentioned above. FIG. 2C shows the effective patient flow waveform, the patient pressure waveform, dQ/dt, and the I/E state signal for a dyssynchronous breath, where flow slope reversals are numbered and equal four. This is a true case of dyssynchrony where all individual slope reversals fulfill the volume criteria mentioned above and hence are reckoned as true slope reversals.

Figure 3A:
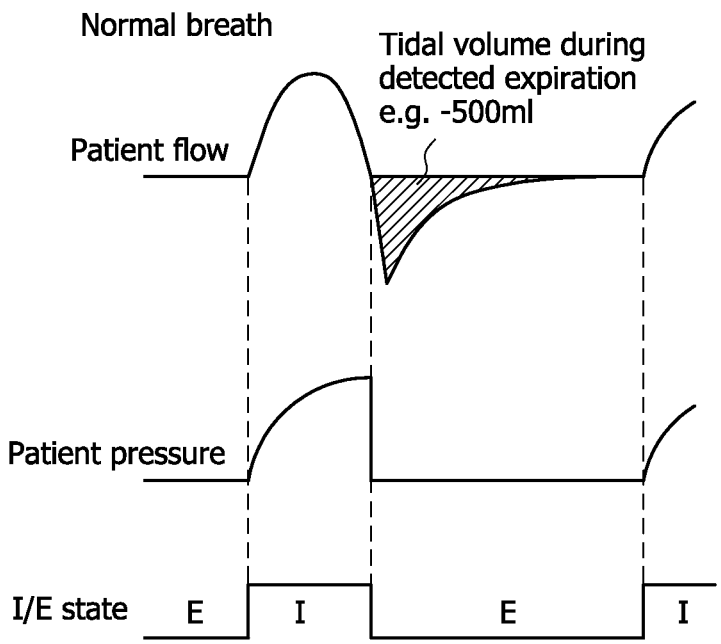
FIGS. 3A and 3B show an effective patient flow waveform, a patient pressure waveform and an I/E state signal for a normal breath and a dyssynchronous breath, respectively, which illustrate a second criterion for detecting dyssynchrony according to an embodiment the invention.
Figure 3B:
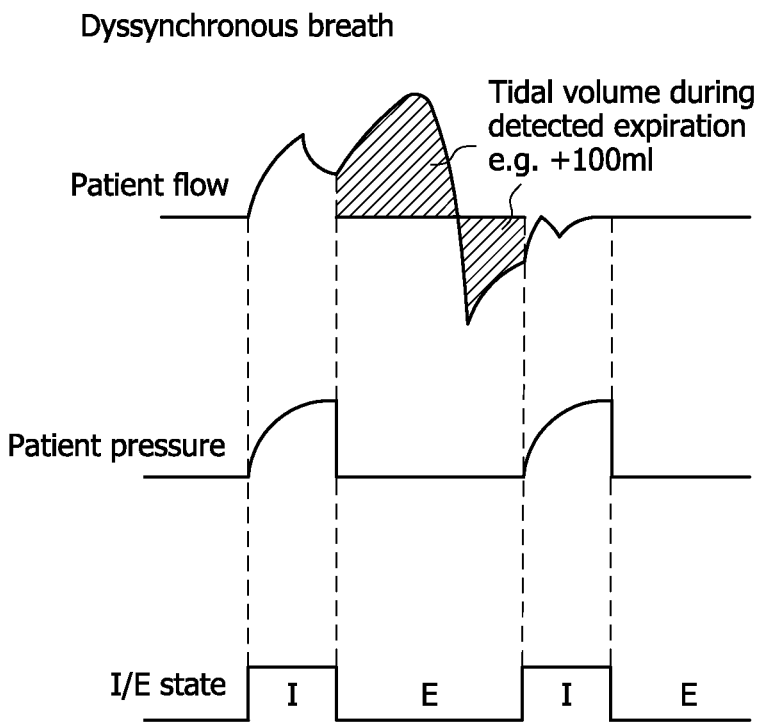

The second criterion is demonstrated in FIGS. 3A and 3B and is based on the incremental tidal volume after onset of the expiratory pressure provided by pressure support system 50 (e.g., EPAP) as indicated by the I/E state signal (in other words, during the expiratory phase as determined by pressure support system 50), and in particular whether such incremental tidal volume is greater than some empirically determined positive number. For convention, it is assumed that positive flows add up to positive tidal volumes and negative flows add up to negative tidal volumes. More specifically, the total flow signal for a breath is examined and the tidal volume for the portion thereof that corresponds to at least a portion of the expiratory phase as determined by pressure support system 50 (i.e., from the beginning of the E for the breath to the end of the E for the breath) is determined (tidal volume is the area under the curve (the integral) of the total flow signal).

In one embodiment, the portion of the expiratory phase that is used begins at a first a predetermined time after the start of the expiratory phase (e.g., approximately 400 ms) and continues for a predetermined duration thereafter (e.g., approximately 500 ms to make the total portion approximately 900 ms long). In another embodiment, the portion of the expiratory phase that is used is the entire expiratory phase. If the incremental tidal volume so determined is greater than the empirically determined positive number, such as, without limitation, 25 ml, then a dyssynchrony condition is declared because such a situation indicates that the patient 54 continued to inspire for a certain empirically determined period after pressure support system 50 has decided to cycle to the expiratory pressure (e.g., EPAP). FIG. 3A shows the effective patient flow waveform, the patient pressure waveform (the pressure provided by pressure support system 50) and the I/E state signal for a normal breath, where the incremental tidal volume during expiration as determined by pressure support system 50 is hatched and equals −500 ml, and FIG. 3B shows the effective patient flow waveform, the patient pressure waveform and the I/E state signal for a dyssynchronous breath, where the incremental tidal volume during expiration as determined by pressure support system 50 is hatched and equals +100 ml.

Figure 4A:
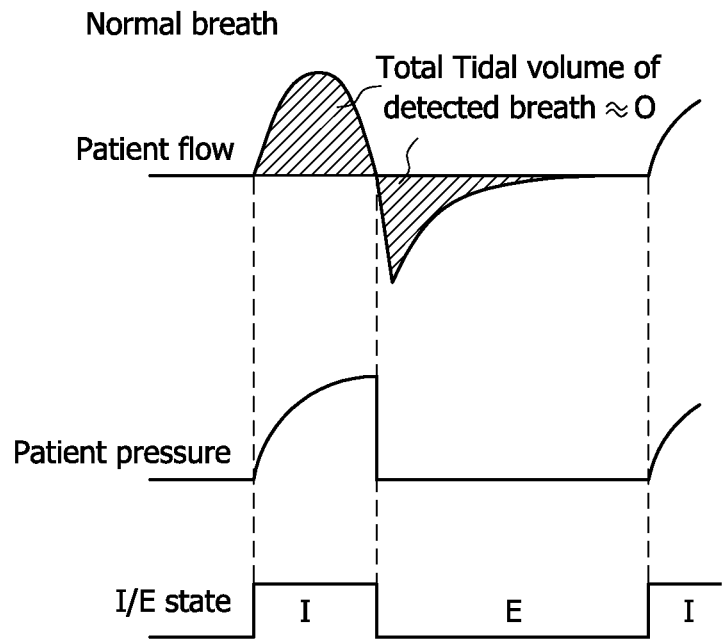
FIGS. 4A and 4B show an effective patient flow waveform, a patient pressure waveform and an I/E state signal for a normal breath and a dyssynchronous breath, respectively, which illustrate a third criterion for detecting dyssynchrony according to an embodiment the invention.
Figure 4B:
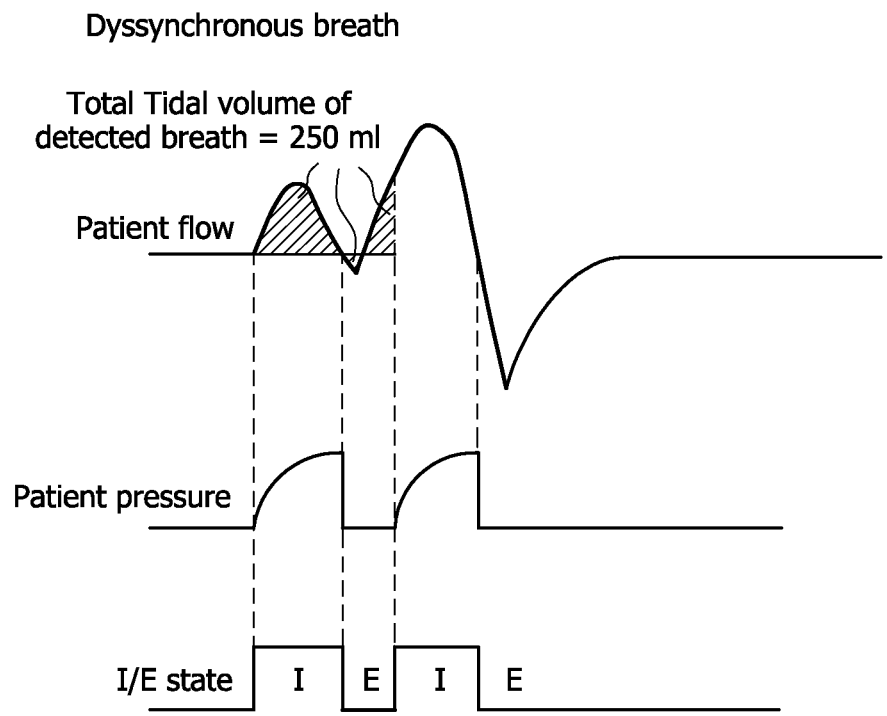

The third criterion is demonstrated in FIGS. 4A and 4B and is based on the absolute value of the total tidal volume during a given breath (as indicated by the I/E state signal). For convention, it is assumed that positive flows add up to positive tidal volumes and negative flows add up to negative tidal volumes. More specifically, the absolute value of the total tidal volume in a breath (as indicated by the I/E state signal; i.e., the beginning of one I, which signals the start of a breath, to the beginning of the next I, which signals the start of a next breath) is determined from the total flow signal. If that number exceeds a certain empirically determined number, such as, without limitation, 800 ml, then a dyssynchrony condition is declared. This is the case because, in an ideal world, the total tidal volume for a breath should approach zero, and a situation where the absolute value of the total tidal volume in a breath is a high positive number indicates that something is wrong with respect to synchronization. For example, patient 54 may be within one large breath cycle for the duration of the I/E state signal indicated cycle, oblivious to a comparatively weak drive provided by pressure support system 50. This kind of dyssynchrony may occur in wakefulness, when the drive of patient 54 swamps the relatively weaker backups provide by pressure support system 50.

FIG. 4A shows the effective patient flow waveform, the patient pressure waveform (the pressure provided by pressure support system 50) and the I/E state signal for a normal breath, where the total tidal volume during a breath as determined by pressure support system 50 is hatched and approaches zero, and FIG. 4B shows the effective patient flow waveform, the patient pressure waveform and the I/E state signal for a dyssynchronous breath, where the total tidal volume during a breath as determined by pressure support system 50 is hatched and equals +250 ml (which in this example is higher than the empirically determined number).

Figure 5A:
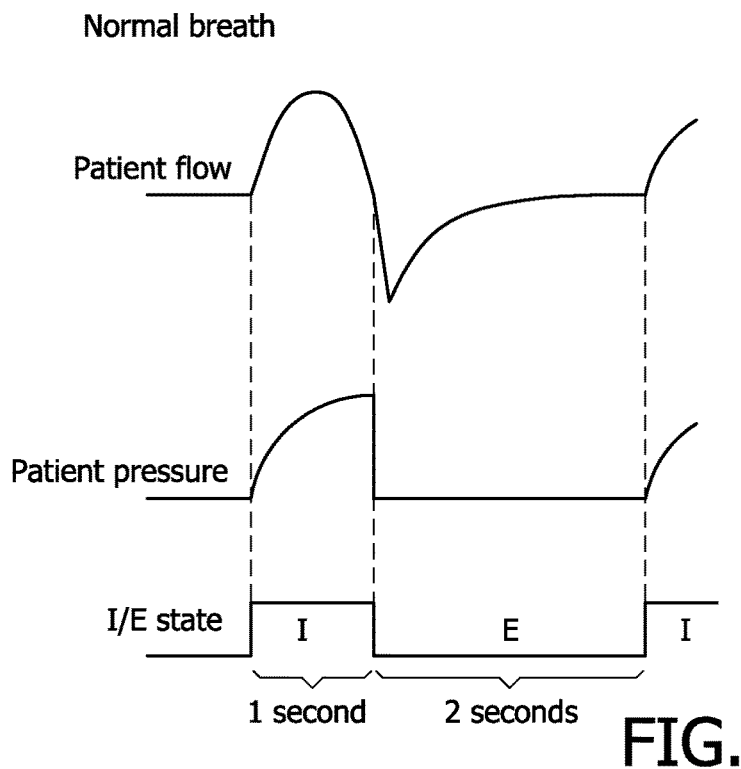
FIGS. 5A and 5B show an effective patient flow waveform, a patient pressure waveform and an I/E state signal for a normal breath and a dyssynchronous breath, respectively, which illustrate a fourth criterion for detecting dyssynchrony according to an embodiment the invention.
Figure 5B:
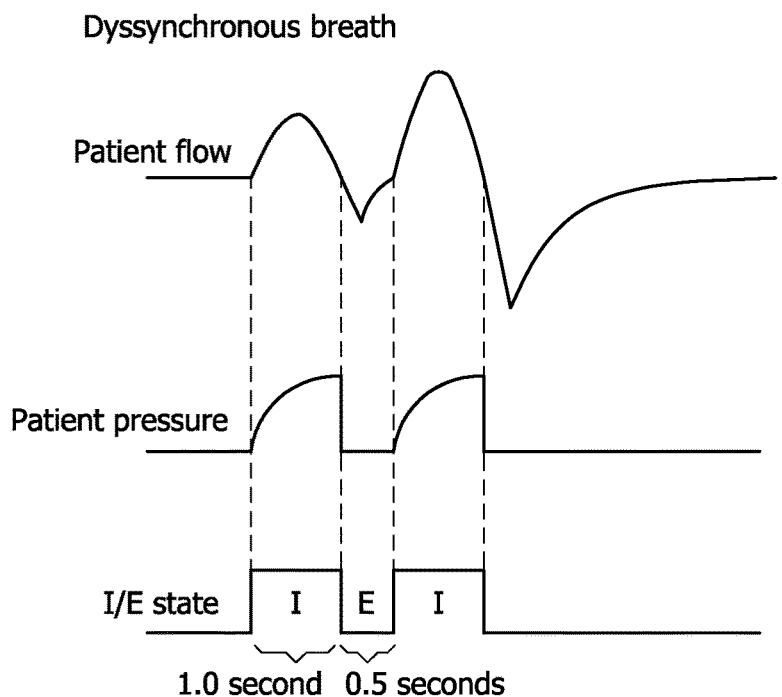

The fourth criterion is demonstrated in FIGS. 5A and 5B and is based on the length (duration) of the expiratory phase in a breath as driven by pressure support system 50 (i.e., the length of the E in the I/E signal for the breath). More specifically, when the next breath begins, the length of the expiratory phase in the prior breath as indicated by the I/E signal is examined and a determination is made as to whether the length was adequate. To do so, in one embodiment, the length of the expiratory phase is compared to an empirically determined percentage (e.g., 75%) of the length (duration) of the inspiratory phase, and if it does not exceed the empirically determined percentage of the length a dyssynchrony condition is declared. In another embodiment, the length of the expiratory phase is compared to an empirically determined duration, such as 1 second, and if it does not exceed the empirically determined duration, a dyssynchrony condition is declared.

FIG. 5A shows the effective patient flow waveform, the patient pressure waveform (the pressure provided by pressure support system 50) and the I/E state signal for a normal breath, where the length of the expiratory phase in the breath as indicated by the I/E signal is 2 seconds (which is higher than the empirically determined 75% of the inspiratory length of 1 second in this example), and FIG. 5B shows the effective patient flow waveform, the patient pressure waveform and the I/E state signal for a dyssynchronous breath, where the length of the expiratory phase in the breath as indicated by the I/E signal is 0.5 seconds (which is lower than the empirically determined 75% of the inspiratory length of 1 second in this example).

This fourth criterion is employed because if pressure support system 50 triggers a breath, cycles to exhalation, and then re-triggers again very soon afterwards, then that is an indication that some odd interaction is going on because patients do not typically breath in, have a very short exhale period, then breathe in again. This may happen very occasionally, but is more often an indication that either one of the two following conditions occurred: (1) pressure support system 50 triggered early or improperly or provided a timed breath right before a patient was to provide a spontaneous breath (this happens in cases where timed breaths are provided but also in cases where expiratory pressure relief (CFlex or BiFlex) is provided and will erroneously declare a spontaneous trigger when the patient's flow bounces slightly positive when they have finished exhaling, before they are ready for the next inhale), or (2) pressure support system 50 cycled early, meaning that the patient had not finished inhaling when we cycled to exhalation (this can be caused by a setting on pressure support system 50 where inhalation is limited to a specific time (especially in the case of a timed breath), or, less commonly, when a spontaneous breath occurs where the patient flow decreases substantially and then increases, sort of as a second "burst" of inhalation). In any case, all of the above are cases where the triggering of pressure support system 50 is not synchronized with the patient's respiratory efforts, which is what the present invention wishes to detect.

Figure 6A:
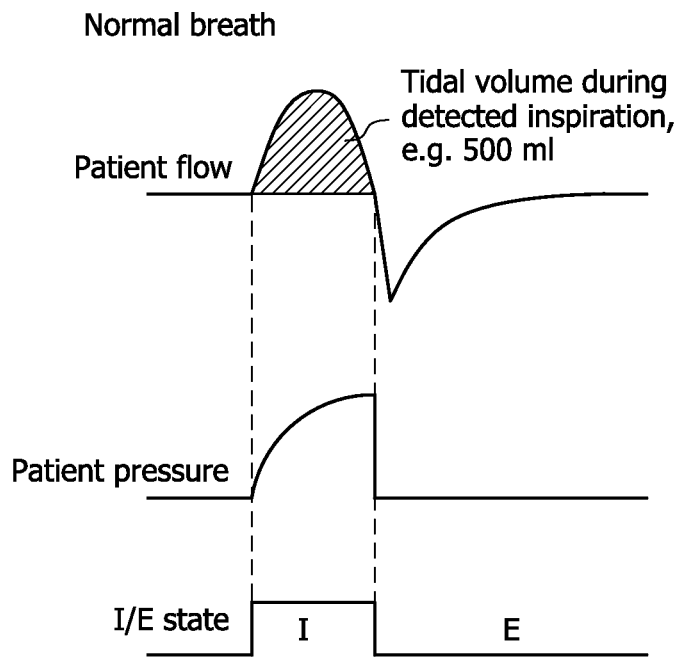
FIGS. 6A and 6B show an effective patient flow waveform, a patient pressure waveform and an I/E state signal for a normal breath and a dyssynchronous breath, respectively, which illustrate a fifth criterion for detecting dyssynchrony according to an embodiment of the invention.
Figure 6B:
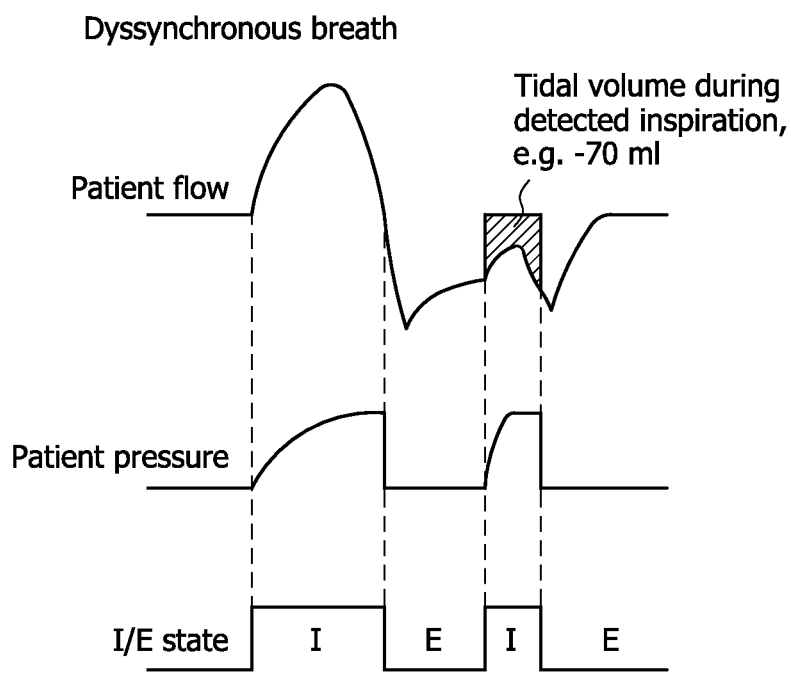

The fifth criterion is demonstrated in FIGS. 6A and 6B and is based on the tidal volume during the inspiratory phase as indicated by the I/E state signal, and in particular whether such inspiratory tidal volume is less than some empirically determined negative number. For convention, it is assumed that positive flows add up to positive tidal volumes and negative flows add up to negative tidal volumes. More specifically, the total flow signal for a breath is examined and the tidal volume for the portion thereof that corresponds to the inspiratory phase as determined by pressure support system 50 (i.e., from the beginning of the I for the breath to the end of the I for the breath) is determined (tidal volume is the area under the curve of the total flow signal). If the inspiratory tidal volume so determined is less than the empirically determined negative number, such as, limitation, −83 ml, then a dyssynchrony condition is declared because such a situation indicates that the patient 54 is expiring for most of the determined inspiratory phase. FIG. 6A shows the effective patient flow waveform, the patient pressure waveform (the pressure provided by pressure support system 50) and the I/E state signal for a normal breath, where the inspiratory tidal volume is hatched and equals 500 ml, and FIG. 6B shows the effective patient flow waveform, the patient pressure waveform and the I/E state signal for a dyssynchronous breath, where the inspiratory tidal volume is hatched and equals −70 ml (which in this example is less than the empirically determined negative number of say −25 ml).

Figure 7:
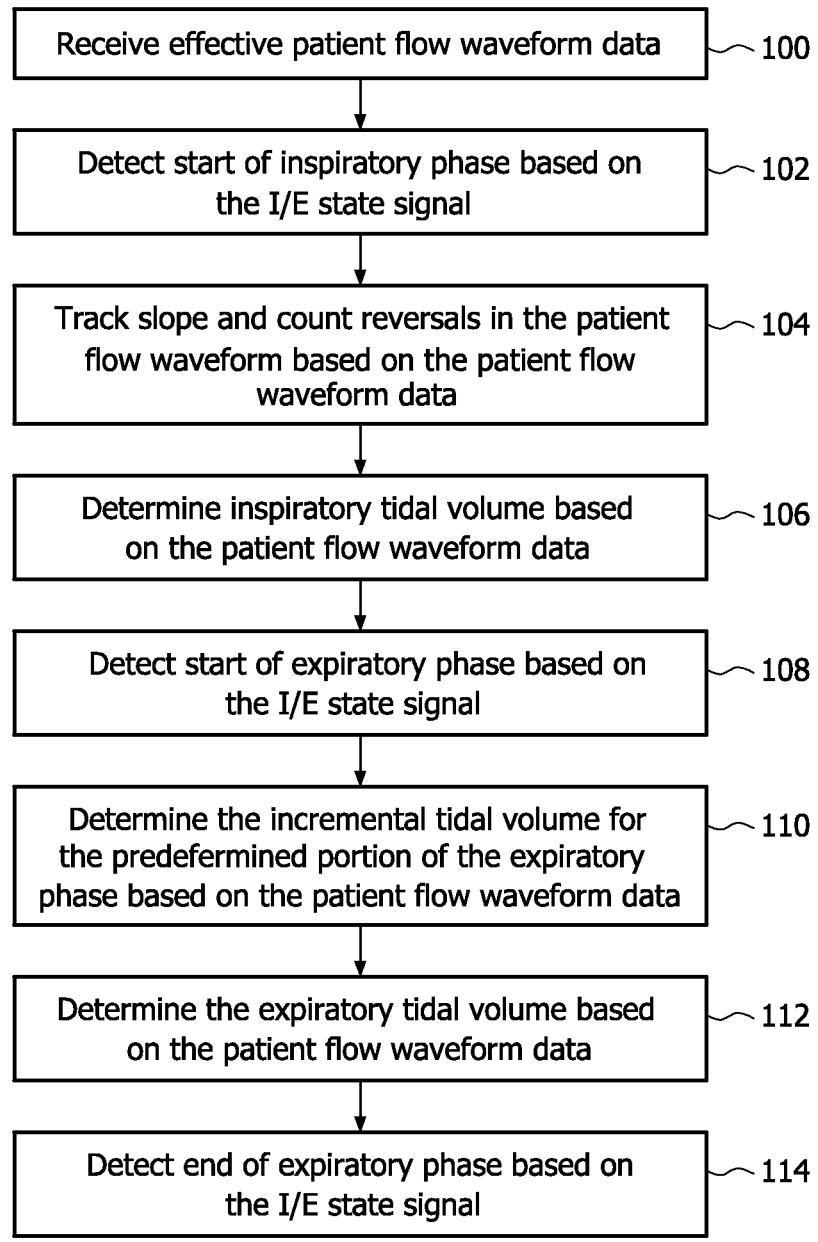
FIG. 7 is a flowchart of a method for detecting dyssynchrony between a pressure support system and a patient according to one particular embodiment of the invention.

FIG. 7 is a flowchart which illustrates of a method for detecting dyssynchrony between pressure support system 50 and patient 54 according to one particular embodiment. The steps shown in FIG. 7 are the steps that are performed for a single breath. As will be appreciated, those steps will be repeated for each breath that is to be monitored. The method shown in FIG. 7 is implemented in and executed by controller 64, typically in the form of software and/or firmware stored in a suitable memory associated with and/or forming a part of controller 64.

The method begins at step 100, wherein the effective patient flow waveform data that is generated based on the $Q_{MEASURED}$ signal is received by the routine or routines of controller 64 that implements the method. As will be appreciated by those of skill in the art, the effective patient flow waveform data may be used to generate the effective patient flow waveforms shown in, for example, FIGS. 2A through 6B. In an exemplary embodiment, the effective patient flow waveform data is generated by sampling the $Q_{MEASURED}$ data at ten samples/second (10 Hz), filtering the sampled data with a fast-acting, single pole, high pass filter, and then smoothing the data as follows: $y(n)=b1*y(n-1)+a0*x(n)-a1(x-1)$, where $b1=31/32$ and $a0=a1=(1+31/32)/2$ (this gives fc=0.05 Hz); $y(n)=y(n-1)/2+x(n)/2$//smoothing. The resulting data is the effective patient flow waveform data used for the computations described herein and is independent of leak estimations.

Following step 100, the method proceeds to step 102, wherein the start of the inspiratory phase is detected based on the I/E state signal. (described elsewhere herein). Next, at step 104, the slope of the effective patient flow waveform is tracked and reversals in the slope of the effective patient flow waveform as described elsewhere herein are counted based on the effective patient flow waveform data being received. At step 106, the inspiratory tidal volume is determined based on the total waveform data. At step 108, the start of the expiratory phase is detected based on the I/E state signal. In step 110, the incremental tidal volume for the predetermined portion of the expiratory phase as described elsewhere herein is determined based on the effective patient flow waveform data. At step 112, the expiratory tidal volume is determined based on the effective patient flow waveform data (this is the total tidal volume for the entire expiratory phase). Finally, at step 114, the end of the expiratory phase is detected based on the I/E state signal.

According to the present invention, a dyssynchrony is declared any time during the process shown in FIG. 7 if any of the criteria described in connection with FIGS. 2A through 6B is determined to be satisfied. In particular, a dyssynchrony will be declared (i) at any time within the breath if the number of volume qualified flow slope reversals is greater than the certain empirically determined number described elsewhere herein; (ii) after the onset of the expiratory pressure, if the incremental tidal volume is greater than the corresponding empirically determined positive number; (iii) at the end of the breath, if the absolute value of the total tidal volume is greater than the certain empirically determined number described elsewhere herein; (iv) at the beginning of the next breath if it is determined that the length of the expiratory phase in the prior breath is inadequate because it does not exceed the empirically determined length described elsewhere herein; or (v) at the end of the inspiratory phase in the breath if the inspiratory tidal volume is less than the corresponding empirically determined negative number as described elsewhere herein.

As noted elsewhere herein, once one or more episodes of dyssynchrony are detected, that information can be used the modify the operation of pressure support system 50 and/or to detect information about patient 54. The modification of the operation of pressure support system 50 may include, without limitation, slowing down the backup rate, reducing the pressure support, turning off a given pressure modality, increasing tidal volumes (if patient 54 is out-pacing the device), adding CFlex, decreasing EPAP. The information that may be detected about patient 54 may include, without limitation, patient wakefulness (sleep state), patient distress, and patient over/under-ventilated.

Figure 8:
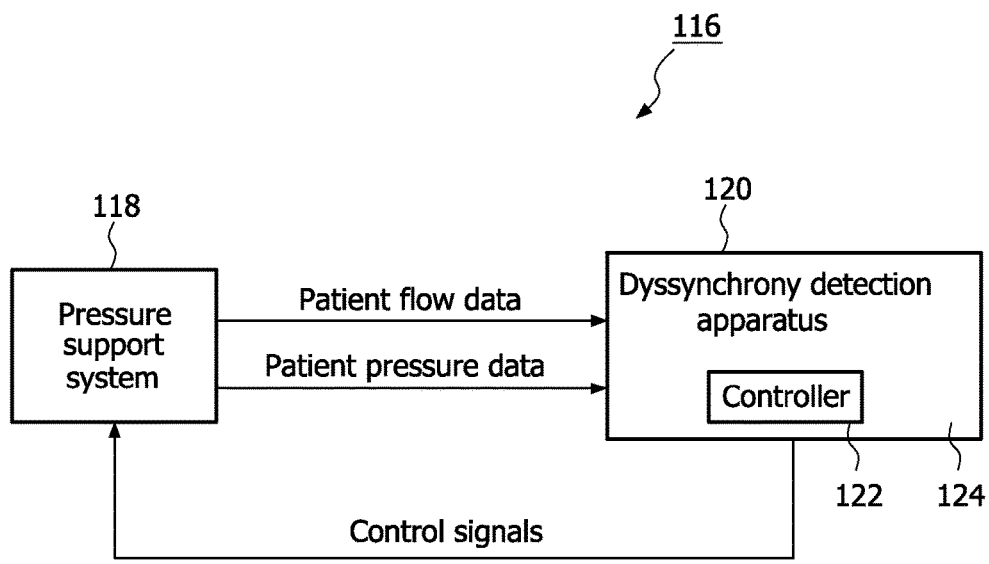
FIG. 8 is a block diagram of a system having a pressure support system and a separate dyssynchrony detection apparatus according to an alternative embodiment of the present invention.

FIG. 8 is a block diagram of a system 116 according to an alternative embodiment of the present invention. The system 116 includes a pressure support system 118 that is similar to pressure support system 50 shown in FIG. 1 and described in detail herein, except that it is not adapted to detect dyssynchrony. Instead, as shown in FIG. 8, pressure support system 118 is operatively coupled to a separate dyssynchrony detection apparatus 120 that is adapted to detect dyssynchrony between pressure support system 118 and the patient using pressure support system 118. In particular, dyssynchrony detection apparatus 120 includes controller 122 provided within a housing 124 that, in the illustrated embodiment, is structured to receive the following data from pressure support system 118: (i) patient flow data relating to the gas flow provided to the patient by pressure support system 118, and (ii) patient pressure data indicating the pressure of the flow of gas provided to the patient by pressure support system 118. In one embodiment, the patient flow data is the effective patient flow waveform data that is described elsewhere herein (and is generated by pressure support system 118). In another embodiment, the patient flow data is the $Q_{MEASURED}$ signal, in which case effective patient flow waveform data may be generated by controller 122 in the manner described hereinabove.

Like controller 62 shown in FIG. 1, controller 122 may be, for example, a microprocessor, a microcontroller or some other suitable processing device, that includes or is operatively coupled to a memory (not shown) that provides a storage medium for data and software executable by controller 122 for controlling the operation of dyssynchrony detection apparatus 120 as described herein. In addition, in the illustrated embodiment, controller 122 is adapted to generate a signal indicating I/E state based on the received patient pressure data using known methods. In response to receiving the patient flow data and the patient pressure data and following the generation of the signal indicating I/E state, controller 122 is further adapted to detect dyssynchrony between pressure support system 118 and the patient based thereon, according to the particular embodiment shown in FIG. 7.

In addition, as seen in FIG. 8, dyssynchrony detection apparatus 120 is structured and adapted to generate and output one or more control signals, which are provided to pressure support system 118, for modifying the operation of pressure support system 118 (e.g., without limitation, change parameters, remove data points from trends, change backup breath rate, and/or modify internal parameters) based on the dyssynchrony information that is generated. Dyssynchrony detection apparatus 120 may be further structured and adapted to output the dyssynchrony information that is generated to a user interface and/or to external media provided as a part of or operatively coupled to dyssynchrony detection apparatus 120. Furthermore, dyssynchrony detection apparatus 120 may be still further structured and adapted to detect information about a patient (e.g., without limitation, patient over/under-ventilated, patient distress, patient sleep state (awake v. asleep), etc.) based on the dyssynchrony information that is generated and to output that information to a user interface and/or to external media provided as a pat of or operatively coupled to dyssynchrony detection apparatus 120.

In an alternative embodiment, rather than generating the signal indicating I/E state in dyssynchrony detection apparatus 120 as described above, dyssynchrony detection apparatus 120 instead receives an I/E state signal from pressure support system 118, and uses that signal to detect dyssynchrony as just described. As still a further alternative, rather than receiving pressure and flow information directly from pressure support system 118 as described above, dyssynchrony detection apparatus 120 may be structured to collect that information on its own using its own pressure and flow instrumentation.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of detecting dyssynchrony between a patient and a pressure support system, comprising:

receiving patient flow data representing a patient flow waveform, the patient flow waveform representing a flow of gas provided to the patient by the pressure support system;

obtaining an I/E state signal indicating whether a current respiratory phase of the patient is inspiratory or expiratory, the I/E state signal being in binary form and having only a first binary state and a second binary state, the first binary state indicating that the current respiratory phase is inspiratory and the second binary state indicating that the current respiratory phase is expiratory; and analyzing both the patient flow data and the I/E state signal for a breath to determine whether at least one of a number of predetermined criterion is satisfied based on both the patient flow data and the I/E state signal and declaring a dyssynchrony for the breath and outputting a dyssynchrony indicator if it is determined that at least one of the number of predetermined criterion is satisfied based on both the patient flow data and the I/E state signal, wherein the dyssynchrony is a condition where a respiratory drive of the patient is out of sync with breaths being generated by the pressure support system, wherein the number of predetermined criterion includes all of; (i) a number of volume qualified flow slope reversals in the patient flow data for the breath exceeding a predetermined number; (ii) an incremented tidal volume during at least a portion of an expiratory phase of the breath as indicated by the I/E state signal exceeding a predetermined positive value; (iii) an absolute value of a tidal volume during the breath exceeds a predetermined value; and (iv) a tidal volume during an inspiratory phase of the breath as indicated by the I/E state is less than a predetermined negative value.

2. The method according to claim 1, wherein the I/E state signal is generated by the pressure support system.

3. The method according to claim 2, wherein the receiving patient flow data, obtaining and analyzing the patient flow data and the I/E signal are performed by the pressure support system.

4. The method according to claim 2, wherein the receiving patient flow data comprises receiving patient flow data in a dyssynchrony detection apparatus separate from the pressure support system, wherein the obtaining an I/E state signal comprises receiving the I/E state signal from the pressure support system in the dyssynchrony detection apparatus, and wherein the analyzing the patient flow data and the I/E signal is performed by the dyssynchrony detection apparatus.

5. The method according to claim 1, wherein the obtaining an I/E state signal comprises receiving pressure data relating to a pressure of the flow of gas provided to the patient by the pressure support system and generating the I/E state signal based on the pressure data.

6. The method according to claim 5, wherein the receiving patient flow data comprises receiving the patient flow data in a dyssynchrony detection apparatus separate from the pressure support system, wherein the receiving pressure data and the generating the I/E state signal comprises receiving the pressure data in the dyssynchrony detection apparatus and generating the I/E state signal in the dyssynchrony detection apparatus, and wherein the analyzing the patient flow data and the I/E signal is performed by the dyssynchrony detection apparatus.

7. The method according to claim 1, further comprising determining a number of volume qualified flow slope reversals present in the patient flow data for an inspiratory phase and an expiratory phase of the breath as indicated by the I/E state signal, wherein the at least one of a number of predetermined criterion is based on the number of volume qualified flow slope reversals, and wherein the declaring a dyssynchrony comprises declaring the dyssynchrony for the breath if it is determined that the number of volume qualified flow slope reversals exceeds a predetermined number.

8. The method according to claim 1, further comprising determining an absolute value of a tidal volume from the patient flow data for an inspiratory phase and an expiratory phase of the breath as indicated by the I/E state signal, wherein the at least one of a number of predetermined criterion is based on the absolute value, and wherein the declaring a dyssynchrony comprises declaring the dyssynchrony for the breath if it is determined that the absolute value of a tidal volume exceeds a predetermined value.

9. The method according to claim 1, further comprising determining a length of an expiratory phase of the breath as indicated by the I/E state signal, wherein the declaring a dyssynchrony further comprises declaring the dyssynchrony for the breath if it is determined that the length of an expiratory phase does not exceed a predetermined percentage of a length of an inspiratory phase of the breath as indicated by the I/E state signal.

10. The method according to claim 1, further comprising determining a length of an expiratory phase of the breath as indicated by the I/E state signal, wherein the declaring a dyssynchrony further comprises declaring the dyssynchrony for the breath if it is determined that the length of an expiratory phase does not exceed a predetermined duration.

11. The method according to claim 1, the declaring a dyssynchrony comprising declaring a plurality of dyssynchronies for a plurality of breaths based on the patient flow data and the I/E state signal, the method further comprising generating a dyssynchrony flag waveform based on the plurality of dyssynchronies.

12. The method according to claim 1, the declaring a dyssynchrony comprising declaring a plurality of dyssynchronies for a plurality of breaths based on the patient flow data and the I/E state signal, the method further comprising modifying operation of the pressure support system based on the plurality of dyssynchronies.

13. The method according to claim 1, the declaring a dyssynchrony comprising declaring a plurality of dyssynchronies for a plurality of breaths based on the patient flow data and the I/E state signal, the method further comprising detecting information about a condition of the patient based on the plurality of dyssynchronies.

14. The method according to claim 1, further comprising modifying operation of the pressure support system based on the declared dyssynchrony.

15. The method according to claim 1, further comprising detecting information about a condition of the patient based on the declared dyssynchrony.

16. A method of detecting dyssynchrony between a patient and a pressure support system, comprising:
receiving patient flow data representing a patient flow waveform, the patient flow waveform representing a flow of gas provided to the patient by the pressure support system;
obtaining an I/E state signal indicating whether a current respiratory phase of the patient is inspiratory or expiratory, the I/E state signal being in binary form and having only a first binary state and a second binary state, the first binary state indicating that the current respiratory phase is inspiratory and the second binary state indicating that the current respiratory phase is expiratory; and
analyzing both the patient flow data and the I/E state signal for a breath to determine whether at least one of a number of predetermined criterion is satisfied based on both the patient flow data and the I/E state signal and declaring a dyssynchrony for the breath and outputting a dyssynchrony indicator if it is determined that at least one of the number of predetermined criterion is satisfied based on both the patient flow data and the I/E state signal, wherein the dyssynchrony is a condition where a respiratory drive of the patient is out of sync with breaths being generated by the pressure support system, further comprising determining an incremental tidal volume from the patient flow data for at least a portion of an expiratory phase of the breath as indicated by the I/E state signal, wherein the at least one of a number of predetermined criterion is based on the incremental tidal volume, and wherein the declaring a dyssynchrony comprises declaring the dyssynchrony for the breath if it is determined that the incremental tidal volume exceeds a predetermined positive value.

17. A method of detecting dyssynchrony between a patient and a pressure support system, comprising:
receiving patient flow data representing a patient flow waveform, the patient flow waveform representing a flow of gas provided to the patient by the pressure support system;
obtaining an I/E state signal indicating whether a current respiratory phase of the patient is inspiratory or expiratory, the I/E state signal being in binary form and having only a first binary state and a second binary state, the first binary state indicating that the current respiratory phase is inspiratory and the second binary state indicating that the current respiratory phase is expiratory; and
analyzing both the patient flow data and the I/E state signal for a breath to determine whether at least one of a number of predetermined criterion is satisfied based on both the patient flow data and the I/E state signal and declaring a dyssynchorny for the breath and outputting a dyssynchorny indicator if it is determined that at least one of the number of predetermined criterion is satisfied based on both the patient flow data and the I/E state signal, wherein the dyssynchorny is a condition where a respiratory drive of the patient is out of sync with breaths being generated by the pressure support system, further comprising determining a tidal volume from the patient flow data for an inspiratory phase of the breath as indicated by the I/E state, wherein the at least one of a number of predetermined criterion is based on the tidal volume, and wherein the declaring a dyssynchrony comprises declaring the dyssynchrony for the breath if it is determined that the tidal volume is less than a predetermined negative value.

18. A pressure support system, comprising:
a pressure generating system adapted to produce a flow of gas;
a patient circuit operatively coupled to the pressure generating system to deliver the flow of gas to an airway of a patient; and a controller operatively coupled to the pressure generating system, the controller being adapted to detect dyssynchrony between the patient and the pressure support system by:

receiving patient flow data representing a patient flow waveform, the patient flow waveform representing the flow of gas provided to the patient by the pressure support system;

receiving an I/E state signal indicating whether a current respiratory phase of the patient is inspiratory or expiratory as determined by the pressure support system, the I/E state signal being in binary form and having only a first binary state and a second binary state, the first binary state indicating that the current respiratory phase is inspiratory and the second binary state indicating that the current respiratory phase is expiratory; and analyzing both the patient flow data and the I/E state signal for a breath to determine whether at least one of a number of predetermined criterion is satisfied based on both the patient flow data and the I/E state signal and declaring a dyssynchrony for the breath and outputting a dyssynchrony indicator if it is determined that at least one of the number of predetermined criterion is satisfied based on both the patient flow data and the I/E state signal, wherein the dyssynchrony is a condition where a respiratory drive of the patient is out of sync with breaths being generated by the pressure support system, wherein the number of predetermined criterion includes all of: (i) a number of volume qualified flow slope reversals in the patient flow data for the breath exceeding a predetermined number; (ii) an incremental tidal volume during at least a portion of an expiratory phase of the breath as indicated by the I/E state signal exceeding a predetermined positive value; (iii) an absolute value of a tidal volume during the breath exceeds a predetermined value; and (iv) a tidal volume during an inspiratory phase of the breath as indicated by the I/E state is less than a predetermined negative value.

19. The pressure support system according to claim 18, wherein the controller is adapted to determine a number of volume qualified flow slope reversals present in the patient flow data for an inspiratory phase and an expiratory phase of the breath as indicated by the I/E state signal, wherein the at least one of a number of predetermined criterion is based on the number of volume qualified flow slope reversals, and wherein the declaring a dyssynchrony comprises declaring the dyssynchrony for the breath if it is determined that the number of volume qualified flow slope reversals exceeds a predetermined number.

20. The pressure support system according to claim 18, wherein the controller is adapted to determine an absolute value of a tidal volume from the patient flow data for an inspiratory phase and an expiratory phase of the breath as indicated by the I/E state signal, wherein the at least one of a number of predetermined criterion is based on the absolute value, and wherein the declaring a dyssynchrony comprises declaring the dyssynchrony for the breath if it is determined that the absolute value exceeds a predetermined value.

21. The pressure support system according to claim 18, wherein the controller is adapted to determine a length of an expiratory phase of the breath as indicated by the I/E state signal, wherein the declaring a dyssynchrony further comprises declaring the dyssynchrony for the breath if it is determined that the length of an expiratory phase does not exceed a predetermined percentage of a length of an inspiratory phase of the breath as indicated by the I/E state signal.

22. The pressure support system according to claim 18, wherein the controller is adapted to determine a length of an expiratory phase of the breath as indicated by the I/E state signal, wherein the declaring a dyssynchrony further comprises declaring the dyssynchrony for the breath if it is determined that the length of an expiratory phase does not exceed a predetermined duration.

23. The pressure support system according to claim 18, the declaring a dyssynchrony comprising declaring a plurality of dyssynchronies for a plurality of breaths based on the patient flow data and the I/E state signal, wherein the controller is further adapted to generate a dyssynchrony flag waveform based on the plurality of dyssynchronies.

24. The pressure support system according to claim 18, the declaring a dyssynchrony comprising declaring a plurality of dyssynchronies for a plurality of breaths based on the patient flow data and the I/E state signal, wherein the controller is further adapted to modify operation of the pressure support system based on the plurality of dyssynchronies.

25. The pressure support system according to claim 18, the declaring a dyssynchrony comprising declaring a plurality of dyssynchronies for a plurality of breaths based on the patient flow data and the I/E state signal, wherein the controller is further adapted to detect information about a condition of the patient based on the plurality of dyssynchronies.

26. A pressure support system, comprising:

a pressure generating system adapted to produce a flow of gas;

a patient circuit operatively coupled to the pressure generating system to deliver the flow of gas to an airway of a patient; and a controller operatively coupled to the pressure generating system, the controller being adapted to detect dyssynchorny between the patient and the pressure support system by;

receiving patient flow data representing a patient flow waveform, the patient flow waveform representing the flow of gas provided to the patient by the pressure support system;

receiving an I/e state signal indicating whether a current respiratory phase of the patient is inspiratory or expiratory as determined by the pressure support system, the I/E state signal being in binary form and having only a first binary state and a second binary state, the first binary state indicating that the current respiratory phase is inspiratory and the second binary state indicating that the current respiratory phase is expiratory; and analyzing both the patient flow data and the I/E state signal for a breath to determine whether at least one of a number of predetermined criterion is satisfied based on both the patient flow data and the I/E state signal and declaring a dyssynchorny for the breath and outputting a dyssynchorny indicator if it is determined that at least one of the number of predetermined criterion is satisfied based on both the patient flow data and the I/E state signal, wherein the dyssynchorny is a condition where a respiratory drive of the patient is out of sync with breaths being generated by the pressure support system, wherein the controller is adapted to determine an incremental tidal volume from the patient flow data for at least a portion of an expiratory phase of the breath as indicated by the I/E state signal, wherein the at least one of a number of predetermined criterion is based on the incremental tidal volume, and wherein the declaring a dyssynchrony comprises declaring the dyssynchrony for the breath if it is determined that the incremental tidal volume exceeds a predetermined positive value.

27. A pressure support system, comprising:
a pressure generating system adapted to produce a flow of gas;
a patient circuit operatively coupled to the pressure generating system to deliver the flow of gas to an airway of a patient; and
a controller operatively coupled to the pressure generating system, the controller being adapted to detect dyssynchorny between the patient and the pressure support system by;
receiving patient flow data representing a patient flow waveform, the patient flow waveform representing the flow of gas provided to the patient by the pressure support system;
receiving an I/E state signal indicating whether a current respiratory phase of the patient is inspiratory or expiratory as determined by the pressure support system, the I/E state signal being in binary form and having only a first binary state and a second binary state, the first binary state indicating that the current respiratory phase is inspiratory and the second binary state indicating that the current respiratory phase is expiratory, and
analyzing both the patient flow data and the I/E state signal for a breath to determine whether at least one of a number of predetermined criterion is satisfied based on both the patient flow data and the I/E state signal and declaring a dyssynchorny for the breath and outputting a dyssynchorny indicator if it is determined that at least one of the number of predetermined criterion is satisfied based on both the patient flow data and the I/E state signal, wherein the dyssynchorny is a condition where a respiratory drive of the patient is out of sync with breaths being generated by the pressure support system, wherein the controller is adapted to determine a tidal volume from the patient flow data for an inspiratory phase of the breath as indicated by the I/E state, wherein the at least one of a number of predetermined criterion is based on the tidal volume, and wherein the declaring a dyssynchrony comprises declaring the dyssynchrony for the breath if it is determined that the tidal volume is less than a predetermined negative value.

28. An apparatus for detecting dyssynchrony between a patient and a pressure support system, comprising:
a housing separate from the pressure support system; and
a controller provided within the housing and operatively coupled to the pressure support system, the controller being adapted to detect dyssynchrony between the patient and the pressure support system by:
receiving patient flow data representing a patient flow waveform, the patient flow waveform representing a flow of gas provided to the patient by the pressure support system;
obtaining an I/E state signal indicating whether a current respiratory phase of the patient is inspiratory or expiratory, the I/E state signal being in binary form and having only a first binary state and a second binary state, the first binary state indicating that the current respiratory phase is inspiratory and the second binary state indicating that the current respiratory phase is expiratory; and
analyzing both the patient flow data and the I/E state signal for a breath to determine whether at least one of a number of predetermined criterion is satisfied based on both the patient flow data and the I/E state signal and declaring a dyssynchrony for the breath and outputting a dyssynchrony indicator if it is determined that at least one of the number of predetermined criterion is satisfied based on both the patient flow data and the I/E state signal, wherein the dyssynchrony is a condition where a respiratory drive of the patient is out of sync with breaths being generated by the pressure support system, wherein the number of predetermined criterion includes all of: (i) a number of volume qualified flow slope reversals in the patient flow data for the breath exceeding a predetermined number; (ii) an incremental tidal volume during at least a portion of an expiratory phase of the breath as indicated by the I/E state signal exceeding a predetermined positive value; (iii) an absolute value of a tidal volume during the breath exceeds a predetermined value; and (iv) a tidal volume during an inspiratory phase of the breath as indicated by the I/E state is less than a predetermined negative value.

29. The apparatus according to claim 28, wherein the receiving patient flow data comprises receiving patient flow data in the apparatus for detecting dyssynchrony from the pressure support system, and wherein the obtaining an I/E state signal comprises receiving the I/E state signal from the pressure support system in the dyssynchrony detection apparatus.

30. The method according to claim 28, wherein the obtaining an I/E state signal comprises receiving pressure data relating to a pressure of the flow of gas provided to the patient by the pressure support system and generating the I/E state signal based on the pressure data.

31. The apparatus according to claim 28, wherein the controller is adapted to determine a number of volume qualified flow slope reversals present in the patient flow data for an inspiratory phase and an expiratory phase of the breath as indicated by the I/E state signal, wherein the at least one of a number of predetermined criterion is based on the number of volume qualified flow slope reversals, and wherein the declaring a dyssynchrony comprises declaring the dyssynchrony for the breath if it is determined that the number of volume qualified flow slope reversals exceeds a predetermined number.

32. The apparatus according to claim 28, wherein the controller is adapted to determine an absolute value of a tidal volume from the patient flow data for an inspiratory phase and an expiratory phase of the breath as indicated by the I/E state signal, wherein the at least one of a number of predetermined criterion is based on the absolute value, and wherein the declaring a dyssynchrony comprises declaring the dyssynchrony for the breath if it is determined that the absolute value exceeds a predetermined value.

33. The apparatus according to claim 28, wherein the controller is adapted to determine a length of an expiratory phase of the breath as indicated by the I/E state signal, wherein the declaring a dyssynchrony comprises declaring the dyssynchrony for the breath if it is determined that the length of an expiratory phase does not exceed a predetermined percentage of a length of an inspiratory phase of the breath as indicated by the I/E state signal.

34. The apparatus according to claim 28, wherein the controller is adapted to determine a length of an expiratory phase of the breath as indicated by the I/E state signal, wherein the declaring a dyssynchrony comprises declaring the dyssynchrony for the breath if it is determined that the length of an expiratory phase does not exceed a predetermined duration.

35. The apparatus according to claim 28, the declaring a dyssynchrony comprising declaring a plurality of dyssynchronies for a plurality of breaths based on the patient flow data and the I/E state signal, wherein the controller is further adapted to generate a dyssynchrony flag waveform based on the plurality of dyssynchronies.

36. The apparatus according to claim 28, the declaring a dyssynchrony comprising declaring a plurality of dyssynchronies for a plurality of breaths based on the patient flow data and the I/E state signal, wherein the controller is further adapted to modify operation of the pressure support system based on the plurality of dyssynchronies.

37. The apparatus according to claim 28, the declaring a dyssynchrony comprising declaring a plurality of dyssynchronies for a plurality of breaths based on the patient flow data and the I/E state signal, wherein the controller is further adapted to detect information about a condition of the patient based on the plurality of dyssynchronies.

38. An apparatus for detecting dyssynchorny between a patient and a pressure support system, comprising:
 a housing separate from the pressure support system; and
 a controller provided within the housing and operatively coupled to the pressure support system, the controller being adapted to detect dyssynchorny between the patient and the pressure support system by:
 receiving patient flow data representing a patient flow waveform, the patient flow waveform representing a flow of gas provided to the patient by the pressure support system,
 obtaining an I/E state signal indicating whether a current respiratory phase of the patient is inspiratory or expiratory, the I/E state signal being in binary form and having only a first binary state and a second binary state, the first binary state indicating that the current respiratory phase is inspiratory and the second binary state indicating that the current respiratory phase is expiratory; and
 analyzing both the patient flow data and the I/E state signal for a breath to determine whether at least one of a number of predetermined criterion is satisfied based on both the patient flow data and the I/E state signal and declaring a dyssynchorny for the breath and outputting a dyssynchorny indicator if it is determined that at least one of the number of predetermined criterion is satisfied based on both the patient flow data and the I/E state signal, wherein the dyssynchorny is a condition where a respiratory drive of the patient is out of sync with breaths being generated by the pressure support system, wherein the controller is adapted to determine an incremental tidal volume from the patient flow data for at least a portion of an expiratory phase of the breath as indicated by the I/E state signal, wherein the at least one of a number of predetermined criterion is based on the incremental tidal volume, and wherein the declaring a dyssynchrony comprises declaring the dyssynchrony for the breath if it is determined that the incremental tidal volume exceeds a predetermined positive value.

39. An apparatus for detecting dyssynchorny between a patient and a pressure support system, comprising:
 a housing separate from the pressure support system; and
 a controller provided within the housing and operatively coupled to the pressure support system, the controller being adapted to detect dyssynchorny between the patient and the pressure support system by:
 receiving patient flow data representing a patient flow waveform, the patient flow waveform representing a flow of gas provided to the patient by the pressure support system;
 obtaining an I/E state signal indicating whether a current respiratory phase of the patient is inspiratory or expiratory, the I/E state signal being in binary form and having only a first binary state and a second binary state, the first binary state indicating that the current respiratory phase is inspiratory and the second binary state indicating that the current respiratory phase is expiratory; and
 analyzing both the patient flow data and the I/E state signal for a breath to determine whether at least one of a number of predetermined criterion is satisfied based on both the patient flow data and the I/E state signal and declaring a dyssynchorny for the breath and outputting a dyssynchorny indicator if it is determined that at least one of the number of predetermined criterion is satisfied based on both the patient flow data and the I/E state signal, wherein the dyssynchorny is a condition where a respiratory drive of the patient is out of sync with breaths being generated by the pressure support system, wherein the controller is adapted to determine a tidal volume from the patient flow data for an inspiratory phase of the breath as indicated by the I/E state, wherein the at least one of a number of predetermined criterion is based on the tidal volume, and wherein the declaring a dyssynchrony comprises declaring the dyssynchrony for the breath if it is determined that the tidal volume is less than a predetermined negative value.

\* \* \* \* \*